United States Patent [19]

Ferrari et al.

[11] Patent Number: 5,543,528
[45] Date of Patent: Aug. 6, 1996

[54] IMIDAZOLINES

[75] Inventors: Bernard Ferrari, Les Matelles; Jëlle Taillades, born Arnaud, Montpellier, both of France

[73] Assignee: Sanofi, Paris, France

[21] Appl. No.: 427,255

[22] Filed: Apr. 24, 1995

Related U.S. Application Data

[62] Division of Ser. No. 34,390, Mar. 18, 1993, Pat. No. 5,434,167.

[30] Foreign Application Priority Data

Mar. 23, 1992 [FR] France .................................. 92 03470

[51] Int. Cl.⁶ ...................... C07D 233/96; C07D 403/06; C07D 409/08; C07D 407/06
[52] U.S. Cl. ........................ 548/301.4; 548/254; 548/253
[58] Field of Search ................................. 548/301.4, 253, 548/254

*Primary Examiner*—David B. Springer
*Attorney, Agent, or Firm*—Bacon & Thomas

[57] ABSTRACT

The invention relates to compounds of the formula

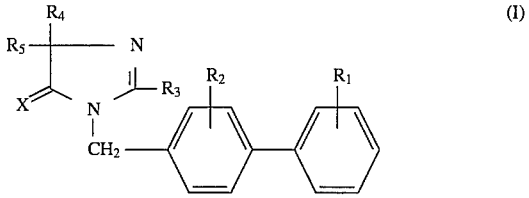

in which:

$R_1$–$R_5$ are defined in the specification, which are useful as angiotensin II antagonists.

14 Claims, No Drawings

IMIDAZOLINES

This application is a divisional of U.S. Ser. No. 08/034,390, filed Mar. 18, 1993, now U.S. Pat. No. 5,434,167.

The present invention relates to imidazoline derivatives N-substituted by a biphenylmethyl group, to their preparation and to the pharmaceutical compositions in which they are present.

The compounds according to the invention antagonize the action of angiotensin II, which is a peptide hormone of the formula H-Asp-Arg-Val-Tyr-Ile-His-Pro-Phe-OH Angiotensin II is a potent vasopressor and the biologically active product of the renin-angiotensin system: renin acts on the angiotensinogen of the plasma to produce angiotensin I, which is converted to angiotensin II by reaction with the angiotensin I converting enzyme.

The compounds of the present invention are nonpeptide compounds which antagonize angiotensin II. By inhibiting the action of angiotensin II on its receptors, the compounds according to the invention prevent especially the increase in blood pressure produced by the hormone-receptor interaction; they also have other physiological actions on the central nervous system.

Thus the compounds according to the invention are useful in the treatment of cardiovascular complaints such as hypertension and heart failure, as well as in the treatment of complaints of the central nervous system and in the treatment of glaucoma and diabetic retinopathy.

European patent application 454 511 describes compounds of the formula

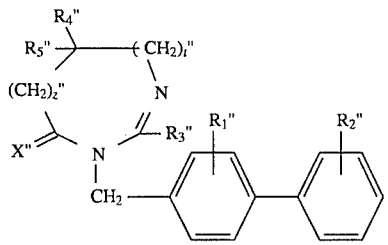

in which:
$R''_1$, $R''_2$, $R''_3$, $R''_4$, $R''_5$, z'' and t'' have different meanings and X'' is an oxygen atom or a sulfur atom.

These compounds are active as angiotensin II antagonists.

The present invention relates to compounds of the formula

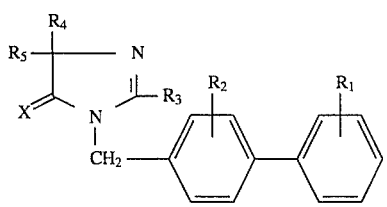

(I)

in which:
$R_1$ and $R_2$ are similar or different and are each independently hydrogen or a group selected from a $C_1$–$C_6$ alkyl, a $C_1$–$C_4$ alkoxy, an amino, an aminomethyl, a carboxyl, an alkoxycarbonyl in which the alkoxy is $C_1$–$C_4$, a cyano, a tetrazolyl, a methylsulfonylamino, a trifluoromethylsulfonylamino, a trifluoromethylsulfonylaminomethyl, an N-cyanoacetamide, an N-hydroxyacetamide, an N-(4-carboxy-1,3-thiazol-2-yl)acetamide, a ureido, a 2-cyanoguanidinocarbonyl, a 2-cyanoguanidinomethyl, an imidazol-1-ylcarbonyl and a 3-cyano-2-methylisothioureidomethyl, with the proviso that at least one of the substituents $R_1$ or $R_2$ is other than hydrogen;

$R_3$ is a hydrogen, a $C_1$–$C_6$ alkyl which is unsubstituted or substituted by one or more halogen atoms, a $C_2$–$C_6$ alkenyl, a $C_3$–$C_7$ cycloalkyl, a phenyl, a phenylalkyl in which the alkyl is $C_1$–$C_3$, or a phenylalkenyl in which the alkenyl is $C_2$–$C_3$, said phenyl groups being unsubstituted or monosubstituted or polysubstituted by a halogen atom, a $C_1$–$C_4$ alkyl, a $C_1$–$C_4$ halogenoalkyl, a $C_1$–$C_4$ polyhalogenoalkyl, a hydroxyl or a $C_1$–$C_4$ alkoxy;

$R_4$ and $R_5$ are each independently a $C_1$–$C_6$ alkyl, a $C_3$–$C_7$ cycloalkyl, a phenyl, or a phenylalkyl in which the alkyl is $C_1$–$C_3$, said alkyl, phenyl or phenylalkyl groups being unsubstituted or substituted by one or more halogen atoms or by a group selected from a $C_1$–$C_4$ perfluoroalkyl, a hydroxyl and a $C_1$–$C_4$ alkoxy;

or $R_4$ and $R_5$ together are either a group of the formula $(CH_2)_n$ or a group of the formula $(CH_2)_p$-$Y(CH_2)_q$, in which Y is either an oxygen atom, or a sulfur atom, or a carbon atom substituted by a $C_1$–$C_4$-alkyl group, a phenyl, or a phenylalkyl in which the alkyl is $C_1$–$C_3$, or a group N-$R_6$, in which $R_6$ is a hydrogen, a $C_1$–$C_4$ alkyl, a phenylalkyl in which the alkyl is $C_1$–$C_3$, a $C_1$–$C_4$ alkylcarbonyl, a $C_1$–$C_4$-halogenoalkylcarbonyl, a $C_1$–$C_4$ polyhalogenoalkylcarbonyl, a benzoyl, an α-aminoacyl or an N-protecting group, or $R_4$ and $R_5$, together with the carbon atom to which they are bonded, form an indane or an adamantane;

$p+q=m$;
n is an integer between 2 and 11;
m is an integer between 2 and 5;
X is a group N-$R_7$ or a group C(CN)$R_s$;
$R_7$ is a $C_1$–$C_4$ alkyl or a cyano group;
$R_8$ is hydrogen, a cyano group, a tetrazolyl group, a tert-butyltetrazolyl group, a phenylsulfonyl group or a group COR$_9$; and
$R_9$ is a thienyl, a furyl, a $C_1$–$C_4$ alkoxy, a phenoxy, a benzyloxy or a phenyl which is unsubstituted or substituted by a halogen, a $C_1$–$C_4$ alkyl or a $C_1$–$C_4$-polyhalogenoalkyl;

and their salts where appropriate.

The compounds of formula (I) in which:
$R_1$ is in the ortho-position and is a carboxyl or a tetrazolyl;
$R_2$ is hydrogen;
$R_3$ is a $C_1$–$C_6$-alkyl;
$R_4$ and $R_5$, together with the carbon to which they are attached, are a group of the formula $(CH_2)_n$;
n is equal to 4 or 5; and
X is a dicyanomethylene group;
and their salts, are preferred compounds of the invention.

The salts of the compounds of formula (I) according to the present invention, where appropriate, include those with mineral or organic acids which permit a suitable separation or crystallization of the compounds of formula (I), such as trifluoroacetic acid, picric acid, oxalic acid or an optically active acid, for example a mandelic acid or a camphosulfonic acid, and acids which form pharmaceutically acceptable salts such as the hydrochloride, the hydrobromide, the sulfate, the hydrogensulfate, the dihydrogenphosphate, the methanesulfonate, the methylsulfate, the maleate, the fumarate and the naphthalene-2-sulfonate.

The salts of compounds of formula (I) also include the salts with organic or mineral bases, for example the salts of alkali or alkaline earth metals, such as the sodium, potassium and calcium salts, the sodium and potassium salts being preferred, or with an amine such as trometamol, or else the salts of arginine, lysine or any pharmaceutically acceptable amine.

According to the present description and in the claims which follow, halogen atom is understood as meaning a bromine, chlorine or fluorine atom; N-protecting group (also designated by Pr) is understood as meaning a group conventionally used in peptide chemistry for temporarily protecting the amine group, for example a Boc, Z or Fmoc group or a benzyl group; esterified carboxyl group is understood as meaning an ester which is labile under appropriate conditions, such as, for example, a methyl, ethyl, benzyl or tert-butyl ester.

The α-aminoacyl group is the residue of a natural amino acid.

The following abbreviations are used in the description and in the Examples:

Et: ethyl
nBu, tBu: n-butyl, tert-butyl
DMF: dimethylformamide
THF: tetrahydrofuran
DCM: dichloromethane
DCC: dicyclohexylcarbodiimide
NBS: N-bromosuccinimide
DIPEA: diisopropylethylamine
HOBT: hydroxybenzotriazole
MeOH: methanol
AcOH: acetic acid
AcOEt: ethyl acetate
ether: ethyl ether
TFA: trifluoroacetic acid
Z: benzyloxycarbonyl
Boc: tert-butoxycarbonyl
BOP: benzotriazolyloxytrisdimethylaminophosphonium hexafluorophosphate
Fmoc: fluorenylmethoxycarbonyl The present invention further relates to the method of preparing the compounds (I). In said method:

a) a heterocyclic derivative of the formula

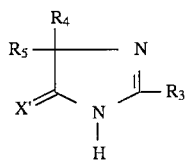

in which $R_3$, $R_4$ and $R_5$ are as defined above for (I) and X' is either a sulfur atom or X as defined for (I), is reacted with a (biphenyl-4-yl)methyl derivative of the formula

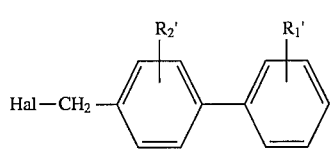

in which Hal is a halogen atom and $R'_1$ and $R'_2$ are respectively either $R_1$ and $R_2$ or a precursor of $R_1$ and/or $R_2$;

b) if appropriate, the resulting compound of the formula

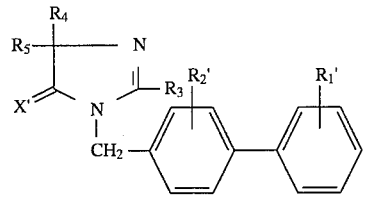

is treated to give the compound (I) by conversion of the groups $R'_1$ and/or $R'_2$ to $R_1$ and/or $R_2$ respectively and the group X' to X; and c) if appropriate, the resulting compound is converted to one of its salts.

The compounds 2 in which X' is X are novel and form part of the invention. Thus the present invention further relates to the compounds of the formula

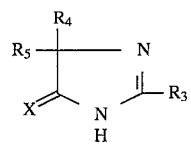

in which $R_3$, $R_4$, $R_5$ and X are as defined above for (I).

The compounds (2) are prepared by known methods from the corresponding 2-imidazoline-5-thiones of the formula

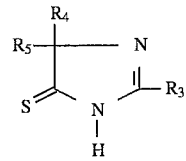

in which $R_3$, $R_4$ and $R_5$ are as defined above for (I).

The compounds 2' can be prepared by the method described in European patent application 454 511: which corresponds to U.S. Pat. No. 5,270,317 it is possible to use the method described by Jacquier et al. (Bull. Soc. Chim. France, 1971, (3), 1040–1051) and to react an alkyl imidate 6 with an amino acid or its ester (5); the resulting compound 7 is then treated with Lawesson's reagent [2,4-bis(4-methoxyphenyl)-1,3-dithia- 2,4-diphosphetane 2,4-disulfide] in accordance with the following reaction scheme:

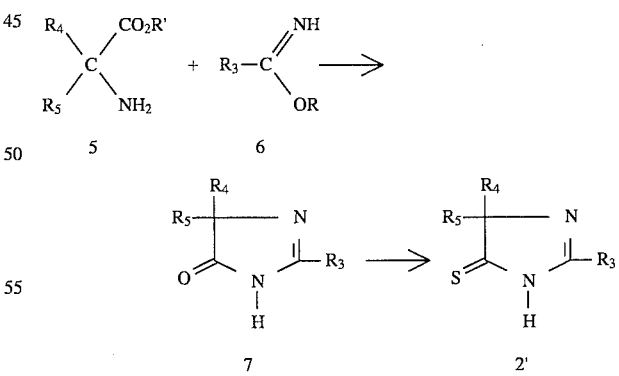

in which R is a $C_1$–$C_4$-alkyl, R' is hydrogen or a $C_1$–$C_4$-alkyl and $R_3$, $R_4$ and $R_5$ are as defined above.

Another possible way of preparing the compound 7 is to react an acid chloride (6'), $R_3COCl$, with a compound 5 in which R' is an amino group.

When $R_4$ and $R_5$ are different, the compounds 2' can be obtained optically pure using methods of asymmetric synthesis or methods of resolving the racemic mixture, such as those described in Synthesis of Optically Active α-Aminoacids, R. M. Williams, Pergamon Press, 1989.

Different methods which can be used to prepare a compound (2) from a compound 2' are reported below.

The preparation of the compounds of formula (2) according to the invention in which X is an imine group which is unsubstituted or substituted by a $C_1$–$C_4$-alkyl or by a cyano group is effected according to J. Marchand-Brynaert in J. Chem. Soc. Chem. Commun., 1983, 818: a primary amine carrying the desired substituent is reacted for example with a compound of formula 2', for example in the presence of mercury diacetate.

The preparation of the compounds of formula (I) according to the invention in which X is an imine group substituted by a $C_1$–$C_4$ alkyl or by a cyano group is preferably effected from compounds 4 in which X' is a sulfur atom; the conversion of a compound 4 to a compound (I) according to the invention is effected by the method of J. Marchand-Brynaert described above.

The preparation of the compounds (2) according to the invention in which X is a cyanomethylene group substituted by another cyano or by a group $COR_9$ is effected using the method described by Z. T. Huang et al. in Chem. Ber., 1968, 119, 2-2219: a compound of the formula $CN-CH_2-CN$ (8) or $CN-CH_2-COR_9$ (8') is reacted with a methylthio derivative of imidazole of the formula

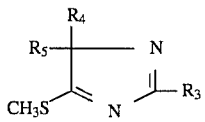

9

According to the same authors, the preparation of the compounds of formula (2) according to the invention in which X is a cyanomethylene group substituted by a phenylsulfonyl can be effected by reacting a compound of the formula

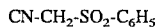

$CN-CH_2-SO_2-C_6H_5$ with a compound of formula 9.

The compound of formula 9 is itself obtained by reacting methyl iodide with the corresponding 2-imidazoline-5-thione (2').

Furthermore, the compounds (I) in which X is a dicyanomethylene group can be prepared according to Y. Tominaga et al. in Heterocycles, 1987, 26 (3), 613: tetracyanoethylene oxide is reacted with a thione group. The reaction can be carried out either on a compound (I) in which X is replaced with a thione group, or on a 2-imidazoline-5-thione (2').

The compounds (2) according to the invention in which X is a group $C(CN)R_8$, $R_8$ being a tetrazolyl or a tert-butyltetrazolyl, are prepared from the corresponding compounds (2) in which $R_8$ is a cyano group by reaction with an azide, for example tributyltin azide.

The compounds of formula (2) according to the invention in which X is a group -CH-CN are prepared from the compounds of formula (2) in which X is -C(CN)CO- $CO_2$ Alk, Alk being a $C_1$–$C_4$ alkyl, by reaction with a strong acid such as trifluoroacetic acid.

The (biphenyl-4-yl)methyl derivative (3) is prepared by a method derived from that described in European patent application 324 377.

Thus the preparation of a compound 3 in which $R'_1$ and/or $R'_2$ is a carboxyl or carboxyester group is described in the patent application cited above.

The methods known in the literature are used to prepare compounds 3 in which $R_1$ and/or $R_2$ are as defined above for (I). These methods are described in European patent application 454 511. The desired group $R_1$ and/or $R'_2$ can also be obtained in the last step of the above-described method from the compound 4 in which $R'_1$ and/or $R'_2$ is a carboxyl group or a derivative of a carboxyl group. Such a compound is prepared from a compound 3 in which $R'_1$ and/or $R'_2$ is a group from which $R_1$ and/or $R_2$ can be prepared.

In the method according to the invention, step a) is carried out in an inert solvent such as DMF, DMSO or THF, in a basic medium, for example in the presence of potassium hydroxide, sodium hydroxide, potassium carbonate, a metal alcoholate, a metal hydride or triethylamine.

The compounds of formula (I) according to the invention in which $R_4$ and $R_5$ together are a group of the formula $(CH_2)_pY(CH_2)_q$ in which Y is a group NH can be prepared by the catalytic hydrogenation of a corresponding compound of formula (I) in which Y is a group N-$R_6$, $R_6$ being a benzyl.

The affinity of the products according to the invention for the angiotensin II receptors was studied in a test for the binding of angiotensin II, labeled with iodine 125, to rat liver membrane receptors. The method used is the one described by S. Keppens et al. in Biochem. J., 1982, 208, 809–817.

The $IC_{50}$, namely the concentration which gives a 50% displacement of the labeled angiotensin II bound specifically to the receptor, is measured. The $IC_{50}$ of the compounds according to the invention is less than $10^{-6}$M.

Also, the effect of the products according to the invention as angiotensin II antagonists was observed on different animal species in which the reninangiotensin system had been activated beforehand (C. Lacour et al., J. Hypertension, 1989, 7 (suppl. 2), S33–S35).

The compounds according to the invention are active after administration by different routes, especially after oral administration.

No signs of toxicity are observed with these compounds at the pharmacologically active doses.

Thus the compounds according to the invention can be used in the treatment of various cardiovascular complaints, especially hypertension, heart failure and venous insufficiency, as well as in the treatment of glaucoma, diabetic retinopathy and various complaints of the central nervous system, for example anxiety, depression, memory deficiencies or Alzheimer's disease.

The present invention further relates to pharmaceutical compositions containing an effective dose of a compound according to the invention, or of a pharmaceutically acceptable salt, and suitable excipients, Said excipients are chosen according to the desired pharmaceutical form and the desired mode of administration.

In the pharmaceutical compositions of the present invention for oral, sublingual, subcutaneous, intramuscular, intravenous, topical, intratracheal, intranasal, transdermal or rectal administration, the active principles of formula (I) above, or their salts where appropriate, can be administered to animals and humans in unit forms of administration, mixed with conventional pharmaceutical carriers, for the prophylaxis or treatment of the above disorders or diseases, The appropriate unit forms of administration include forms for oral administration, such as tablets, gelatin capsules, powders, granules and solutions or suspensions to be taken orally, forms for sublingual, buccal, intratracheal or intranasal administration, forms for subcutaneous, intramuscular or intravenous administration and forms for rectal administration. For topical application, the compounds according to the invention can be used in creams, ointments or lotions.

To achieve the desired prophylactic or therapeutic effect, the dose of active principle can vary between 0.01 and 50 mg per kg of body weight per day.

Each unit dose can contain from 0.5 to 1000 mg, preferably from 1 to 500 mg, of active ingredients in combination with a pharmaceutical carrier. This unit dose can be administered 1 to 5 times a day so as to administer a daily dosage of 0.5 to 5000 mg, preferably 1 to 2500 mg.

When a solid composition in the form of tablets is prepared, the active ingredient is mixed with a pharmaceutical vehicle such as gelatin, starch, lactose, magnesium stearate, talc, gum arabic or the like. The tablets can be coated with sucrose, a cellulose derivative or other appropriate substances, or else they can be treated so as to have a sustained or delayed activity and so as to release a predetermined amount of active principle continuously.

A preparation in the form of gelatin capsules is obtained by mixing the active ingredient with a diluent and pouring the resulting mixture into soft or hard gelatin capsules.

A preparation in the form of a syrup or elixir or for administration in the form of drops can contain the active ingredient in conjunction with a sweetener, which is preferably calorie-free, and methylparaben and propylparaben as antiseptics, as well as a flavoring and an appropriate color.

The water-dispersible granules or powders can contain the active ingredient mixed with dispersants or wetting agents, or suspending agents such as polyvinylpyrrolidone, as well as with sweeteners or taste correctors.

Rectal administration is effected using suppositories prepared with binders which melt at the rectal temperature, for example cacao butter or polyethylene glycols.

Parenteral administration is effected using aqueous suspensions, isotonic saline solutions or sterile and injectable solutions which contain pharmacologically compatible dispersants and/or wetting agents, for example propylene glycol or butylene glycol.

The active principle can also be formulated as microcapsules, with one or more carriers or additives if appropriate.

In addition to the products of formula (I) above or one of their pharmaceutically acceptable salts, the compositions of the present invention can contain other active principles such as, for example, tranquilizers or other drugs which can be useful in the treatment of the disorders or diseases indicated above.

Thus the present invention relates to pharmaceutical compositions containing several active principles in association, one being a compound according to the invention and it being possible for the other or others to be a beta-blocking compound, a calcium antagonist, a diuretic, a non-steroidal antiinflammatory or a tranquilizer.

The following Examples illustrate the invention without however implying a limitation. The following abbreviations are used in these Examples:

RT denotes room temperature. $KHSO_4$-$K_2SO_4$ denotes an aqueous solution containing 16.6 g of potassium bisulfate and 33.3 g of potassium sulfate per liter. In general, the saline solutions employed are aqueous solutions.

The melting points (m.p.$_c$) are given in degrees Celsius; unless indicated otherwise, they are measured without recrystallization of the product.

The purity of the products is checked by thin layer chromatography (TLC) or HPLC (high performance liquid chromatography). The products are characterized by their NMR spectra run at 200 MHz in deuterated DMSO, the internal reference being tetramethylsilane, unless indicated otherwise.

The following abbreviations are used in the interpretation of the NMR spectra:

s: singlet
sb: broad singlet
d: doublet
t: triplet
q: quadruplet
quint: quintuplet
sext: sextuplet
m: unresolved signals or multiplet The compounds of formula (I) according to the invention in which X is a group $C(CN)R_8$, $R_8$ being as defined above for (I), exhibit cis-trans isomerism around the methylene bond when $R_8$ is other than CN.

It is generally possible to observe the presence of the 2 isomers in equilibrium; for certain meanings of $R_8$, however, one of the forms may be preponderant.

The isomers can be studied either by coalescence in NMR at high temperature or by N.O.E.S.Y. $^1$H NMR (Nuclear Overhauser Effect Spectroscopy) in 2 dimensions. Such a phenomenon has been described for enamino ketones and enamino acids by O. Michinori in Methods in Stereochemical Analysis of Dynamic NMR Spectroscopy to Organic Chemistry.

EXAMPLE 1

N-Isopropyl-2-n-butyl-1-[(2'-carboxybiphenyl-4-yl)methyl]-4-spirocyclopentane-2-imidazolin-5-imine trifluoroacetate (I, X=NCH(CH$_3$)$_2$)

This compound is prepared from 2-n-butyl-4-spirocyclopentane- 1-[(2'-tert-butoxycarbonylbiphenyl-4-yl)methyl]-2-imidazoline-5-thione. This 2-imidazoline-5-thione, hereafter called compound A, is described in European patent application 454 511.

The thione is converted to the N-isopropylimine according to J. Marchand-Brynaert et al. in J. Chem. Soc. Chem. Commun., 1983, 818.

A solution of 150 mg of the 2-imidazoline-5-thione (compound A) in 4 ml of DCM is treated with 1 ml of isopropylamine in the presence of mercury diacetate and the mixture is stirred for 5 days at RT. After filtration on Célite®, the filtrate is concentrated and the residue is taken up in 50 ml of ethyl acetate. After washing with 20 ml of a saturated solution of sodium chloride, drying over sodium sulfate and concentration, the residue is purified by chromatography on silica using a toluene/ethyl acetate mixture (3/1, v/v) as the eluent. The oil obtained (50 mg) is treated with a TFA/DCM mixture (3 ml/3 ml) for 1 hour at RT to give the expected compound in the form of a clear oil.
Mass spectrum: MH$^+$: 446
NMR spectrum: 0.8 ppm: t: 3 H: CH$_3$ (nBu) 1 and 1.1 ppm: 2 d: 6 H: (CH$_3$)$_2$CHN=1.2–2.2 ppm: m: 12 H: cyclopentane and CH$_3$-CH$_2$-CH$_2$-CH$_2$- 2.45 ppm: t: 2 H: CH$_3$-CH$_2$-CH$_2$-CH$_2$- 3.9 ppm: m: 1 H: (CH$_3$)$_2$CH-N=5.05 ppm: s: CH$_2$-C$_6$H$_4$- 6.9–8.1 ppm: m: 8 H: aromatic The NMR spectrum indicates the presence of a mixture of syn and anti isomers of the N-(isopropyl)imine group.

EXAMPLE 2

2-n-Butyl-1-[(2'-carboxybiphenyl-4-yl)methyl]-5-dicyanomethylene-4-spirocyclopentane-2-imidazoline trifluoroacetate

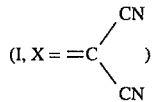

A) 2-n-Butyl-5-dicyanomethylene-4-spirocyclopentane-1-[(2'-tert-butoxycarbonylbiphenyl-4-yl)methyl]-2-imidazoline A solution of 518 mg of compound A of example 1 in 17 ml of anhydrous benzene is treated with 156 mg of tetracyano-ethylene oxide for 5 hours at RT under argon. The reaction medium is concentrated and chromatographed on silica using a toluene/AcOEt mixture (97/3, v/v) as the eluent to give 200 mg of the expected product in the form of an oil.

NMR spectrum: 1.0 ppm: t: 3 H: $CH_3$ (nBu) 1.35 ppm: s: 9 H: tBu 1.5 ppm: sext: 2 H: $CH_3$-$CH_2$-$CH_2$-$CH_2$- 1.8 ppm: quint: 2 H: $CH_3$-$CH_2$-$CH_2$-$CH_2$- 1.9–2.25 ppm: m: 8 H: cyclopentane 2.55 ppm: t: 2 H: $CH_3$-$CH_2$-$CH_2$-$CH_2$- 5.4 ppm: s: 2 H: $CH_2$-$C_6H_4$- 7.15–7.95 ppm: m: 8 H: aromatic B) 2-n-Butyl-1-[(2'-carboxybiphenyl-4-yl)methyl]-5-dicyanomethylene-4-spirocyclopentane-2-imidazoline trifluoroacetate 180 mg of the oil obtained are treated with a DCM/TFA mixture (10 ml/10 ml) for 1 hour at RT. After concentration, the residue is triturated in an ether/hexane mixture. The yellow solid obtained is filtered off and dried under vacuum.

m=170 mg

Mass spectrum: $MH^+$: 453

NMR spectrum: 0.8 ppm: t: 3 H: $CH_3$ (nBu) 1.25 ppm: sext: 2 H: $CH_3$-$CH_2$-$CH_2$-$CH_2$- 1.5 ppm: quint: 2 H: $CH_3$-$CH_2$-$CH_2$-$CH_2$- 1.8–2.5 ppm: m: 10 H: cyclopentane+$CH_3$-$CH_2$-$CH_2$-$CH_2$- 5.3 ppm: s: 2 H: $CH_2$-$C_6H_4$- 7.05–7.7 ppm: m: 8 H: aromatic

EXAMPLE 3

2-n-Butyl-5-dicyanomethylene-4-spirocyclopentane-1-[(2'-(tetrazol-5-yl)biphenyl-4-yl)methyl]-2-imidazoline

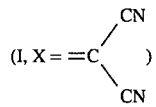

A) 2-n-Butyl-4-spirocyclopentane-2-imidazoline-5-thione

This compound is prepared from 2-n-butyl-4-spirocyclopentane-2-imidazolin-5-one, described in European patent application 454 511, by reaction with Lawesson's reagent [2,4-bis(4-methoxyphenyl)-1,3-dithia-2,4-diphosphetane 2,4-disulfide].

7.58 g of the 2-imidazolin-5-one in the form of the base are dissolved in 50 ml of toluene under nitrogen. 7.90 g of Lawesson's reagent are added and the mixture is refluxed for 2 hours. It is concentrated to dryness and the residue is purified by chromatography on silica using a DCM/AcOEt mixture (9/1, v/v) as the eluent to give 5.95 g of the expected product.

M.p.$_c$= 96° C.

NMR spectrum: 0.8 ppm: t: 3 H: $CH_3$ (nBu) 1.2 ppm: sext: 2 H: $CH_3$-$CH_2$-$CH_2$-$CH_2$- 1.4–1.8 ppm: m: 10 H: cyclopentane+$CH_3$-$CH_2$-$CH_2$-$CH_2$- 2.35 ppm: t: 2 H: $CH_3$-$CH_2$-$CH_2$-$CH_2$- 5.3 ppm: s: 1H: NH B) 2-n-Butyl-5-dicyanomethylene-4-spirocyclopentane-2-imidazoline 1 g of the compound prepared in the previous step is dissolved in 50 ml of anhydrous benzene under nitrogen. 686 mg of tetracyanoethylene oxide are added and the mixture is stirred for 1 hour at RT. The precipitate formed is filtered off and then dried under vacuum and purified by chromatography on silica using a heptane/ethyl acetate mixture (2/8, v/v) as the eluent. The product obtained is triturated in ether and then filtered off.

m=510 mg

M.p.$_c$=145° C.

NMR spectrum: 1 ppm: t: 3 H: $CH_3$ (nBu) 1.2 ppm: sext: 2 H: $CH_3$-$CH_2$-$CH_2$-$CH_2$- 1.7 ppm: quint: 2 H: $CH_3$-$CH_2$-$CH_2$-$CH_2$- 1.8–2.4 ppm: m: 8 H: cyclopentane 2.6 ppm: t: 2 H: $CH_3$-$CH_2$-$CH_2$-$CH_2$- 11.4 ppm: s: 1 H: NH C) 2-n-Butyl-5-dicyanomethylene-4-spirocyclopentane-1-[(2'-(trityltetrazol-5-yl)biphenyl-4-yl)methyl]-2-imidazoline A mixture containing 70 mg of 80% sodium hydride in oil and 10 ml of DMF is placed under nitrogen and 500 mg of the compound prepared in step B), dissolved in 10 ml of anhydrous DMF, are added dropwise. After stirring for 20 minutes at RT, 1.2 g of 4-bromomethyl-2'-(triphenylmethyltetrazol-5-yl)biphenyl are added and the mixture is stirred for 4 hours at 40° C. under nitrogen. After concentration of the medium, the residue is taken up in AcOEt. The organic phase is washed with water, a saturated solution of NaCl, a 5% $KHSO_4$-$K_2SO_4$ solution and then a saturated solution of NaCl. It is dried and concentrated and the oil obtained is then purified by chromatography on silica using a heptane/ethyl acetate mixture (7/3, v/v) as the eluent. The product obtained crystallizes from ethyl acetate.

m=700 mg

D) 2-n-Butyl-5-dicyanomethylene-4-spirocyclopentane-1-[(2'-(tetrazol-5-yl)biphenyl-4-yl)methyl]-2-imidazoline 700 mg of the product obtained in the previous step are placed in 10 ml of 5% acetic acid in methanol and the mixture is refluxed for 24 hours. It is concentrated to dryness and the residue is then purified by chromatography on silica using a DCM/AcOEt/AcOH mixture (90/10/10) as the eluent. The product obtained is triturated in ether; the precipitate formed is filtered off and dried under vacuum.

m=180 mg

M.p.$_c$=181° C.

Mass spectrum: $MH^+$: 477

NMR spectrum: 0.8 ppm: t: 3 H: $CH_3$ (nBu) 1.25 ppm: sext: 2 H: $CH_3$-$CH_2$-$CH_2$-$CH_2$- 1.5 ppm: quint: 2 H: $CH_3$-$CH_2$-$CH_2$-$CH_2$- 1.8–2.4 ppm: m: 10 H: cyclopentane+$CH_3$-$CH_2$-$CH_2$-$CH_2$- .5.3 ppm: s: 2 H: $CH_2$-$C_6H_4$- 7.0–7.8 ppm: m: 8 H: aromatic

EXAMPLE 4

2-n-Butyl-5-(1-cyano-1-ethoxycarbonylmethylene)-1-[(2'-carboxybiphenyl-4-yl)methyl]-4-spirocyclopentane-2-imidazoline

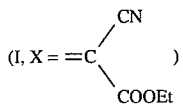

A) 2-n-Butyl-5-methylthio-4-spirocyclopentaneimidazole 3 g of 2-n-butyl-4-spirocyclopentane-2-imidazoline-5-thione, described in Example 3, step A), are placed in 50 ml of anhydrous THF under nitrogen and 470 mg of 80% sodium hydride in oil are added in small portions. After stirring for 20 minutes at RT under nitrogen, 900 µl of methyl iodide are added and the mixture is stirred under nitrogen for 4 hours. 20 ml of water are added and the reaction medium is then concentrated. The oil obtained is taken up in 100 ml of ethyl acetate and then washed with water, a saturated solution of NaCl, a saturated solution of $NaHCO_3$ and a saturated solution of NaCl; it is dried over sodium sulfate and concentrated.

m=3.2 g

NMR spectrum: 1 ppm: t: 3 H: $CH_3$ (nBu) 1.4 ppm: sext: 2 H: $CH_3$-$CH_2$-$CH_2$-$CH_2$- 1.6–2 ppm: m: 10 H: cyclopentane+$CH_3$-$CH_2$-$CH_2$-$CH_2$- 2.6 ppm: t: 2 H: $CH_3$-$CH_2$-$CH_2$-$CH_2$- 2.65 ppm: s: 3 H: $SCH_3$-

B) 2-n-Butyl-5-(1-cyano-1-ethoxycarbonylmethylene)-4-spirocyclopentane-2-imidazoline A mixture containing 1 g of the product prepared in the previous step and 476 µl of ethyl cyanoacetate is heated at 100° C. for 6 hours. The oil obtained is purified by chromatography on silica using a DCM/acetone mixture (100/1, v/v) as the eluent.

m=1 g

NMR spectrum: 0.85 ppm: t: 3 H: $CH_3$ (nBu) 1.15–1.4 ppm: m: 5 H: $CH_3$ (Et)+$CH_3$-$CH_2$-$CH_2$-$CH_2$- 1.45–2.3 ppm: m: 10 H: cyclopentane+$CH_3$-$CH_2$-$CH_2$-$CH_2$- 2.45 ppm: t: 2 H: $CH_3$-$CH_2$-$CH_2$-$CH_2$- 4.2 ppm: q: 2 H: $CH_2$ (Et) 11.4 ppm: s: 1 H: NH C) 2-n-Butyl-5-(1-cyano-1-ethoxycarbonylmethylene)-4-spirocyclopentane-1-[(2'-tert-butoxycarbonylbiphenyl-4-yl)methyl]-2-imidazoline 114 mg of 80% sodium hydride in oil, suspended in 5 ml of anhydrous DMF, are placed under argon. 1 g of the compound prepared in step B) in 5 ml of anhydrous DMF is added and the mixture is stirred for 20 minutes at RT under nitrogen. 1.32 g of 4-bromomethyl- 2'-tert-butoxycarbonylbiphenyl are added and the mixture is stirred under nitrogen for 2 hours at RT and for 4 hours at 60° C. It is concentrated, the residue is taken up in 50 ml of ethyl acetate and the organic phase is then washed with water, a 5% $KHSO_4$-$K_2SO_4$ solution, a saturated solution of NaCl, a saturated solution of $NaHCO_3$ and a saturated solution of NaCl. It is dried and concentrated and the oil obtained is then purified by chromatography on silica using a heptane/AcOEt mixture (9/1, v/v) as the eluent.

m=860 mg

D) 2-n-Butyl-5-(1-cyano-1-ethoxycarbonylmethylene)-1-[(2'-carboxybiphenyl-4-yl)methyl]-4-spirocyclopentane-2-imidazoline 800 g of the product obtained in the previous step are dissolved in 10 ml of a TFA/DCM mixture (5/5, v/v) and stirred at RT for 3 hours. The solution is concentrated to dryness and the oil obtained is then co-evaporated twice with ether. The oil is then triturated in ether and the precipitate formed is filtered off and dried under vacuum. The residue is purified by chromatography on silica using a DCM/AcOEt/AcOH mixture (90/10/2, v/v/v) as the eluent.

m=240 mg

M.p.$_c$=102° C.

Mass spectrum: $MH^+$: 500.2

NMR spectrum: 0.9 ppm: t: 3 H: $CH_3$ (nBu) 1.2–2.8 ppm: m: 17 H: cyclopentane+$CH_3$ (Et)+$CH_3$-$CH_2$-$CH_2$-$CH_2$- 4.2 ppm: m: 2 H: -$OCH_2$-$CH_3$ 5.3 and 5.6 ppm: 2 s: 2 H: $CH_2$-$C_6H_4$- 7–7.9 ppm: m: 8 H: aromatic The NMR spectrum indicates that the cis and trans forms of the methylene are in equilibrium.

EXAMPLES 5 AND 6

2-n-Butyl-1-[(2'-carboxybiphenyl-4-yl)methyl]-5-(1-cyano-1-tert-butoxycarbonylmethylene)-4-spirocyclopentane- 2-imidazoline

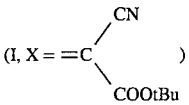

and 2-n-butyl-1-[(2'-carboxybiphenyl-4-yl)methyl]-5-(1-cyanomethylene)-4-spirocyclopentane-2-imidazoline (I, X==CHCN)

A) 2-n-Butyl-5-(1-cyano-1-tert-butoxycarbonylmethylene)-4-spirocyclopentane-2-imidazoline This compound is prepared by the method described in Example 4, step B), by reacting tert-butyl cyanoacetate with the compound prepared in Example 4, step A).

NMR spectrum: 0.85 ppm: t: 3 H: $CH_3$ (nBu) 1.35 ppm: sext: 2 H: $CH_3$-$CH_2$-$CH_2$-$CH_2$- 1.45–2.35 ppm: m: 19 H: tBu+cyclopentane+$CH_3$-$CH_2$-$CH_2$-$CH_2$- 2.5 ppm: t: 2 H: $CH_3$-$CH_2$-$CH_2$-$CH_2$- 11.4 ppm: s: 1 H: NH B) 2-n-Butyl-5-(1-cyano-1-tert-butoxycarbonylmethylene)-4-spirocyclopentane-1-[(2'-tert-butoxycarbonylbiphenyl-4-yl)methyl]-2-imidazoline This compound is prepared by the method described in Example 4, step C).

NMR spectrum: 0.8 ppm: m: 3 H: $CH_3$ (nBu) 1–2.6 ppm: m: 32 H: 2 tBu+cyclopentane+$CH_3$-$CH_2$-$CH_2$-$CH_2$- 5.3 and 5.45 ppm: 2 s: 2 H: $CH_2$-$C_6H_4$- 6.95–7.7 ppm: m: 8 H: aromatic C) 2-n-Butyl-1-[(2'-carboxybiphenyl-4-yl)methyl]-5-(1-cyano-1-tert-butoxycarbonylmethylene)-4-spirocyclopentane-2-imidazoline This compound is obtained by reacting TFA with the compound described in Example 4, step D). The oil obtained is purified by chromatography on silica using a heptane/AcOEt/AcOH mixture (60/40/1.5, v/v/v) as the eluent. 2 products are separated out.

1st product:

Mass spectrum: $MH^+$: 528

NMR spectrum: 0.8 ppm: m: 3 H: $CH_3$ (nBu) 1.2–2.5 ppm: m: 14 H: $CH_3$-$CH_2$-$CH_2$-$CH_2$-+cyclopentane 5.3 and 5.4 ppm: 2 s : 2 H: $CH_2$-$C_6H_4$- 6.9–7.8 ppm: m: 8 H: aromatic The NMR spectrum (2 s at 5.3 and 5.4 ppm) indicates the presence of both the cis and trans forms of the methylene in equilibrium.

2nd product:

Mass spectrum: $MH^+$: 428

NMR spectrum: 0.8 ppm: m: 3 H: CH₃ (nBu) 1.2–2.4 ppm: m: 14 H: CH₃-CH₂-CH₂-CH₂-+cyclopentane 4.6 and 4.8 ppm: 2 s: 2 H: CH₂-C₆H₄- 6.9–7.7 ppm: m: 9 H: aromatic+=CHCN The NMR spectrum indicates the presence of both the cis and trans forms of the methylene.

EXAMPLES 7 AND 8

2-n-Butyl-1-[(2'-carboxybiphenyl-4-yl)methyl]-5-(1-cyano- 1-(tert-butyltetrazol-5-yl)methylene)-4-spirocyclopentane- 2-imidazoline hemiacetate

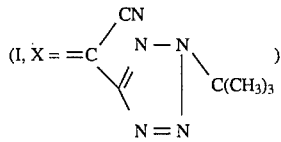

and 2-n-butyl-1-[(2'-carboxybiphenyl-4-yl)methyl]-5-(1-cyano-1-(tetrazol-5-yl)methylene)-4-spirocyclopentane-2-imidazoline

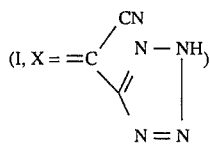

A) 2-n-Butyl-5-(1-cyano-1-(tetrazol-5-yl)methylene)-4-spirocyclopentane-1-[(2'-tert-butoxycarbonylbiphenyl-4-yl)methyl]-2-imidazoline 740 mg of the compound prepared in Example 2, step A), are placed in 10 ml of xylene and the mixture is treated with 1.5 g of tributyltin azide for 48 hours under reflux. After concentration, the medium is taken up in an ether/5% sodium hydroxide mixture (20/20, v/v) and stirred for 15 minutes at RT. The aqueous phase is decanted and the ether phase is extracted with 30 ml of 5% sodium hydroxide. The aqueous phases are washed with ether and then acidified to pH 2 by the addition of concentrated hydrochloric acid. The brown gum obtained is extracted with 100 ml of AcOEt. The organic phase is washed with a saturated solution of sodium chloride and then dried over sodium sulfate. After filtration and concentration, the brown foam obtained is purified by chromatography on silica using a heptane/acetone/AcOH mixture (80/20/1, v/v/v) as the eluent.

The expected product is obtained in the form of an oil.
m=450 mg
IR (DCM): 2200 cm⁻¹ (CN)
NMR spectrum: 0.8 ppm: m: 3 H: CH₃ (nBu) 1–2.4 ppm: m: 23 H: tBu+cyclopentane+CH₂-CH₂-CH₂-CH₃ 4.9 and 5.4 ppm: 2 s: CH₂-C₆H₄ 6.4–7.6 ppm: m: 8 H: aromatic B) 2-n-Butyl-1-[(2'-carboxybiphenyl-4-yl)methyl]-5-(1-cyano- 1-(tert-butyltetrazol-5-yl)methylene)-4-spirocyclopentane- 2-imidazoline hemiacetate 400 mg of the compound obtained in the previous step are dissolved in a DCM/TFA mixture (5/10, v/v) and stirred for 3 hours at RT. After concentration to dryness, the residue is triturated in an ether/hexane mixture (1/9, v/v) and the solid phase obtained is filtered off and dried under vacuum. It is purified by chromatography on silica using a DCM/MeOH/AcOH mixture (100/2/1, v/v/v) as the eluent. A first compound is isolated. This is triturated in an ether/hexane mixture (1/9, v/v) and then filtered off to give the expected product in the form of a white powder.

m=160 mg
M.p.c= 210°–212° C.
NMR spectrum: 0.75 ppm: t: 3 H: CH₃ (nBu) 1.2 ppm: sext: 2 H: CH₃-CH₂-CH₂-CH₂- 1.4–2.4 ppm: m: 21 H: tBu+ cyclopentane+CH₃-CH₂-CH₂-CH₂- 4.8 and 5.3 ppm: 2 s: 2 H: -CH₂-C₆H₄- 6.4–7.6 ppm: m: 8 H: aromatic C) 2-n-Butyl-1-[(2'-carboxybiphenyl-4-yl)methyl]-5-(1 -cyano-1-(tetrazol-5-yl)methylene)-4-spirocyclopentane-2-imidazoline The chromatography performed in step B) enables a second compound to be isolated. This is obtained in the form of a white powder after trituration in an ether/hexane mixture (1/1, v/v) and filtration.

m=220 mg
M.p.c=217°–219° C.
NMR spectrum: 0.85 ppm: t: 3 H: CH₃ (nBu) 1.3 ppm: sext: 2 H: CH₃-CH₂-CH₂-CH₂- 1.6 ppm: quint: 2 H: CH₃-CH₂-CH₂-CH₂- 1.8–2.6 ppm: m: 10 H: cyclopentane+CH₃-CH₂-CH₂-CH₂- 4.9 and 5.4 ppm: 2 s : 2 H: -CH₂-C₆H₄- 6.4–7.7 ppm: m: 8 H: aromatic 12.7 ppm: s: 1 H: CO₂H The NMR spectra of Examples 7 and 8 show the existence of the cis and trans forms of the methylene in equilibrium. For the compound of Example 7, the position of the t-butyl group on the tetrazole is not determined; the structural formula shown above is therefore arbitrary.

EXAMPLE 9

5-(1-Benzoyl-1-cyanomethylene)-2-n-butyl- 1-[(2'-carboxybiphenyl- 4-yl)methyl]-4-spirocyclopentane-2-imidazoline trifluoroacetate

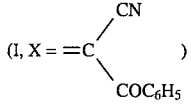

A) 5-(1-Benzoyl-1-cyanomethylene)-2-n-butyl-4-spirocyclopentane- 2-imidazoline 2 g of the compound prepared in Example 4, step A), and 1.30 g of benzoylacetonitrile are dissolved in the minimum volume of DCM and the solution is heated at 100° C. for 8 hours, with stirring. The oil obtained is chromatographed on silica using a heptane/AcOEt mixture (8/2, v/v) as the eluent to give 1.63 g of the expected product.
NMR spectrum: 0.95 ppm: t: 3 H: CH₃ (nBu) 1.4 ppm: sext: 2 H: CH₃-CH₂-CH₂-CH₂- 1.65 ppm: quint: 2 H: CH₃-CH₂-CH₂-CH₂- 1.7–2.7 ppm: m: 10 H: cyclopentane+ CH₃-CH₂-CH₂-C₂- 7.4–8.0 ppm: m: 5 H: aromatic 12.4 ppm: s: 1 H: NH B) 5-(1-Benzoyl-1-cyanomethylene)-2-n-butyl-4-spirocyclopentane- 1-[(2'-tert-butoxycarbonylbiphenyl-4yl)methyl]-2-imidazoline 800 mg of the imidazoline prepared in the previous step, 700 mg of potassium carbonate and 1.8 g of 4-bromomethyl-2'-tert-butoxycarbonylbiphenyl are dissolved in 20 ml of anhydrous DMF under nitrogen. The reaction medium is heated at 70° C. for 5 hours, with stirring. Extraction is carried out with AcOEt and the organic phase is washed with water and then with a saturated solution of sodium chloride. The product obtained is chromatographed on silica using a heptane/AcOEt mixture (8/2, v/v) as the eluent to give 820 mg of the expected product.

C) 5-(1-Benzoyl-1-cyanomethylene)-2-n-butyl-1-[(2'-carboxybiphenyl- 4-yl)methyl]-4-spirocyclopentane-2-imidazoline trifluoroacetate 720 mg of the product obtained in the previous step are treated with 10 ml of TFA in 10 ml of DCM for 4 hours at RT, with stirring. After concentration to dryness, the residue is triturated in ether and the solution obtained is concentrated to give the expected product in the form of a foam.
NMR spectrum: 0.9 ppm: t: 3 H: $CH_3$ (nBu) 1.4 ppm: sext: 2 H: $CH_3$-$CH_2$-$CH_2$-$CH_2$- 1.7 ppm: quint: 2 H: $CH_3$-$CH_2$-$CH_2$-$CH_2$- 1.8–2.5 ppm: m: 8 H: cyclopentane 2.75 ppm: t: 2 H: $CH_3$-$CH_2$-$CH_2$-$CH_2$- 4.8 ppm and 5 ppm: s: 2 H: -$CH_2$-$C_6H_4$- 6.6–7.8 ppm: m: 13 H: aromatic The NMR spectrum indicates the presence of both the cis and trans forms of the methylene.

EXAMPLE 10

2-n-Butyl-1-[(2'-carboxybiphenyl-4-yl)methyl]-5-(1-cyano-1-methoxycarbonylmethylene)-4-spirocyclopentane- 2-imidazoline trifluoroacetate

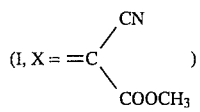

A) 2-n-Butyl-5-(1-cyano-1-methoxycarbonylmethylene)-4-spirocyclopentane- 2-imidazoline This compound is prepared by reacting methyl cyanoacetate with the compound prepared in Example 4, step A), following the method described in Example 9, step A).
NMR spectrum: 0.9 ppm: t: 3 H: $CH_3$ (nBu) 1.35 ppm: sext: 2 H: $CH_3$-$CH_2$-$CH_2$-$CH_2$- 1.6 ppm: quint: 2 H: $CH_3$-$CH_2$-$CH_2$-$CH_2$- 1.65–2.4 ppm: m: 8 H: cyclopentane 2.55 ppm: t: 2 H: $CH_3$-$CH_2$-$CH_2$-$CH_2$- 3.8 ppm: s: 3 H: $OCH_3$ 11.4 ppm: s: 1 H: NH B) 2-n-Butyl-1-[(2'-carboxybiphenyl-4-yl)methyl]-5-(1-cyano-1-methoxycarbonylmethylene)-4-spirocyclopentane-2-imidazoline trifluoroacetate The expected compound is prepared by following the method described in Example 9, steps B) and C). This compound crystallizes from hexane to which a small amount of ether has been added.
M.p.$_c$=52°–55° C.
NMR spectrum: 1.8 ppm: t: 3 H: $CH_3$ (nBu) 1.2–2.6 ppm: m: 14 H: cyclopentane+$CH_3$-$CH_2$-$CH_2$-$CH_2$- 3.6 ppm: d: 3 H: $CH_3O$- 5.2 and 5.4 ppm: 2 s: 2 H: -$CH_2$-$C_6H_4$- 6.8–7.7 ppm: m: 8 H: aromatic The NMR spectrum indicates the presence of both the cis and trans forms of the substituted methylene in equilibrium.

EXAMPLE 11

5-(1-Benzyloxycarbonyl-1-cyanomethylene)-2-n-butyl-1-[(2'-carboxybiphenyl-4-yl)methyl]-4-spirocyclopentane- 2-imidazoline

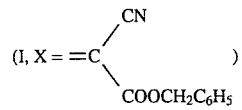

A) 5-(1-Benzyloxycarbonyl-1-cyanomethylene)-2-n-butyl-4-spirocyclopentane-2-imidazoline This compound is prepared by reacting benzyl cyanoacetate with the compound prepared in Example 4, step A), following the method described in Example 9, step A). The compound obtained crystallizes from an ether/hexane mixture.

M.p.$_c$= 91° C.
NMR spectrum: 0.8 ppm: t: 3 H: $CH_3$ (nBu) 1.25 ppm: sext: 2 H: $CH_3$-$CH_2$-$CH_2$-$CH_2$- 1.5 ppm: quint: 2 H: $CH_3$-$CH_2$-$CH_2$-$CH_2$- 1.6–2.2 ppm: m: 8 H: cyclopentane 5.15 ppm: s: 2 H: $OCH_2$-$C_6H_5$ 11.4 ppm: s: 1 H: NH B) 5-(1-Benzyloxycarbonyl-1-cyanomethylene)-2-n-butyl-1-[(2'-carboxybiphenyl-4-yl)methyl]-4-spirocyclopentane-2-imidazoline The expected compound is obtained by following the method described in Example 9, steps B) and C). It crystallizes from a hexane/ether mixture.
M.p.$_c$=92° C.
NMR spectrum: 0.75 ppm: q: 3 H: $CH_3$ (nBu) 1.1–2.4 ppm: m: 14 H: cyclopentane+$CH_3$-$CH_2$-$CH_2$-$CH_2$- 5 ppm: split s: 2 H: $OCH_2$-$C_6H_5$ 5.2 and 5.4 ppm: 2 s: 2 H: -$CH_2$-$C_6H_4$- 6.8–7.65 ppm: m: 13 H: aromatic The NMR spectrum indicates that the cis and trans forms of the methylene are in equilibrium.

EXAMPLE 12

2-n-Butyl-1-[(2'-carboxybiphenyl-4-yl)methyl]-5-[1-cyano-1-(fur-2-ylcarbonyl)methylene]-4-spirocyclopentane- 2-imidazoline

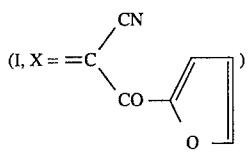

A) 2-n-Butyl-5-[1-cyano-1-(fur-2-ylcarbonyl)methylene]-4-spirocyclopentane-2-imidazoline This compound is prepared by adding furoylacetonitrile to the compound prepared in Example 4, step A), following the method described in Example 9, step A).
NMR spectrum; 0.95 ppm: t: 3 H: $CH_3$ (nBu) 1.4 ppm: sext: 2 H: $CH_3$-$CH_2$-$CH_2$-$CH_2$- 1.65 ppm: quint: 2 H: $CH_3$-$CH_2$-$CH_2$-$CH_2$- 1.7–2.5 ppm: m: 8 H: cyclopentane 2.6 ppm: t: 2 H: $CH_3$-$CH_2$-$CH_2$-$CH_2$- 6.8 ppm: q: 1 H: furyl 7.6 ppm: d: 1 H: furyl 8.1 ppm: d: 1 H: furyl 12.4 ppm: s: 1 H: NH B) 2-n-Butyl-1-[(2'-carboxybiphenyl-4-yl)methyl]-5-[1-cyano-1-(fur-2-ylcarbonyl)methylene]-4-spirocyclopentane-2-imidazoline The expected compound is obtained by following the method described in Example 9, steps B) and C). This compound crystallizes from an ether/hexane mixture.
M.p.$_c$=159° C.
Mass spectrum: $MH^+$: 522
NMR spectrum: 0.8 ppm: t: 3 H: $CH_3$ (nBu) 1.3 ppm: sext: 2 H: $CH_3$-$CH_2$-$CH_2$-$CH_2$- 1.6 ppm: quint: 2 H: $CH_3$-$CH_2$-$CH_2$-$CH_2$- 1.7–2.4 ppm: m: 8 H: cyclopentane 2.6 ppm: t: 2 H: $CH_3$-$CH_2$-$CH_2$-$CH_2$- 4.9 ppm: s: 2 H: -$CH_2$-$C_6H_4$- 6.4–7.8 ppm: m: 11 H: aromatic+furyl The NMR spectrum indicates the presence of only one form (cis or trans) of the substituted methylene.

EXAMPLE 13

2-n-Butyl-1-[(2'-carboxybiphenyl-4-yl)methyl]-5-[1
-cyano-1-(thien-2-ylcarbonyl)methylene]-
4-spirocyclopentane-2-imidazoline

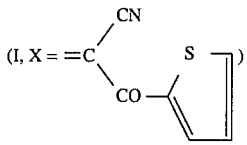

A) 2-n-Butyl-5-[1-cyano-1-(thien-2-ylcarbonyl)methylene]-4-spirocyclopentane-2-imidazoline This compound is prepared by reacting thienoylacetonitrile with the compound prepared in Example 4, step A), following the method described in Example 9, step A). The product obtained crystallizes from an ether/hexane mixture.
M.p.$_c$=86°–89° C.
NMR spectrum: 0.85 ppm: t: 3 H: CH$_3$ (nBu) 1.3 ppm: sext: 2 H: CH$_3$-CH$_2$-CH$_2$-CH$_2$- 1.55 ppm: quint: 2 H: CH$_3$-CH$_2$-CH$_2$-CH$_2$- 1.8–2.4 ppm: m: 8 H: cyclopentane+CH$_3$-CH$_2$-CH$_2$-CH$_2$- 7.2 ppm: q: 1 H: thienyl 7.95 ppm: q: 1 H: thienyl 8.15 ppm: d: 1 H: thienyl 12.3 ppm: s: 1 H: NH B) 2-n-Butyl-1-[(2'-carboxybiphenyl-4-yl)methyl]-5-[1-cyano-1-(thien-2-ylcarbonyl)methylene]-4-spirocyclopentane-2-imidazoline The expected compound is prepared by following the method described in Example 9, steps B) and C). This compound crystallizes from an ether/hexane mixture.
M.p.$_c$= 162° C.
NMR spectrum: 0.9 ppm: t: 3 H: CH$_3$ (nBu) 1.4 ppm: sext: 2 H: CH$_3$-CH$_2$-CH$_2$-CH$_2$- 1.65 ppm: quint: 2 H: CH$_3$-CH$_2$-CH$_2$-CH$_2$- 1.8–2.4 ppm: m: 8 H: cyclopentane 2.7 ppm: t: 2 H: CH$_3$-CH$_2$-CH$_2$-CH$_2$- 5 ppm: s: 2 H: -CH$_2$-C$_6$H$_4$- 6.6–8.0 ppm: m: 11 H: aromatic+thienyl The NMR spectrum indicates the presence of only one form (cis or trans) of the substituted methylene.

EXAMPLE 14

2-n-Butyl-1-[(2'-cyanobiphenyl-4-yl)methyl]-5-
[1,1-dicyanomethylene]-4-spirocyclopentane-
2-imidazoline and
2-n-butyl-5-[1-cyano-1-(tetrazol-5-yl)methylene]-4
-spirocyclopentane-1-[(2'-(tetrazol-5-yl)biphenyl-
4-yl)methyl]-2-imidazoline

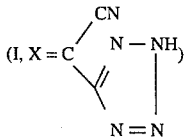

A) 2-n-Butyl-5-[1,1-dicyanomethylene]-4-spirocyclopentane- 2-imidazoline

This compound is the one prepared in Example 4, step B). It can also be prepared by reacting malononitrile with the compound prepared in Example 4, step A), following the method described in Example 9, step A). The product obtained crystallizes from ether.
M.p.$_c$= 145° C. B) 2-n-Butyl-1-[(2'-cyanobiphenyl-4-yl)methyl]-5-[1,1-dicyanomethylene]-4-spirocyclopentane-2-imidazoline 1.05 g of the compound of step A), 1.2 g of potassium carbonate and 2.3 g of 4-bromomethyl-2'-cyanobiphenyl (prepared according to European patent application 324 377) are mixed in 10 ml of anhydrous DMF. The mixture is heated at 70° C. for 24 hours, with stirring. It is concentrated to dryness, the residue is then extracted with ethyl acetate and the organic phase is then washed with water and with a saturated solution of sodium chloride. The product is purified by chromatography on silica using a heptane/AcOEt mixture (7/3, v/v) as the eluent.
NMR spectrum: 0.8 ppm: t: 3 H: CH$_3$ (nBu) 1.2 ppm: sext: 2 H: CH$_3$-CH$_2$-CH$_2$-CH$_2$- 1.5 ppm: quint: 2 H: CH$_3$-CH$_2$-CH$_2$-CH$_2$- 1.8–2.5 ppm: m: 10 H: cyclopentane+CH$_3$-CH$_2$-CH$_2$-CH$_2$- 5.35 ppm: s: 2 H: -CH$_2$-C$_6$H$_4$- 7.2–8.0 ppm: m: 8 H: aromatic C) 2-n-Butyl-5-[1-cyano-1-(tetrazol-5-yl)methylene]-4 -spirocyclopentane-1-[(2'-(tetrazol-5-yl)biphenyl-4 -yl)methyl]-2-imidazoline A mixture containing 1.58 g of the compound prepared in the previous step, 3 ml of tributyltin chloride and 760 mg of sodium azide in 15 ml of xylene is prepared and refluxed for 60 hours. The reaction medium is taken up in an ether/5% sodium hydroxide mixture (50/50, v/v) and stirred for 15 minutes at RT. After decantation, the aqueous phase is acidified to pH 1 by the addition of hydrochloric acid. The gum formed is extracted by the addition of AcOEt. The organic phase is concentrated, the residue is taken up in ether and the mixture is chromatographed on silica using as the eluent a mixture of DCM, MeOH and ammonia containing 20% of water (85/15/1.6, v/v/v). 1 g of the expected product is obtained.
Mass spectrum: MH$^+$: 520
NMR spectrum: 0.75 ppm: t: 3 H: CH$_3$ (nBu) 1.2 ppm: sext: 2 H: CH$_3$-CH$_2$-CH$_2$-CH$_2$- 1.45 ppm: quint: 2 H: CH$_3$-CH$_2$-CH$_2$-CH$_2$- 1.8–2.4 ppm: m: 10 H: cyclopentane+CH$_3$-CH$_2$-CH$_2$-CH$_2$- 4.6 ppm: s: 2 H: -CH$_2$-C$_{6H4}$- 6.4–7.8 ppm: m: 8 H: aromatic The NMR spectrum indicates the presence of one form (cis or trans) of the substituted methylene.

EXAMPLE 15

2-n-Butyl-1-[(2'-carboxybiphenyl-4-yl)methyl]-5-
(1-cyano- 1-phenylsulfonylmethylene)-4-
spirocyclopentane-2-imidazoline

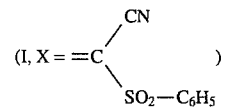

A) 2-n-Butyl-5-(1-cyano-1-phenylsulfonylmethylene)-4 -spirocyclopentane-2-imidazoline This compound is prepared by reacting phenylsulfonylacetonitrile with the compound prepared in Example 4, step A), following the method described in Example 9, step A).
NMR spectrum: 0.85 ppm: t: 3 H: CH$_3$ (nBu) 1.2 ppm: sext: 2 H: CH$_3$-CH$_2$-CH$_2$-CH$_2$- 1.6 ppm: quint: 2 H: CH$_3$-CH$_2$-CH$_2$-CH$_2$- 1.7–2.4 ppm: m: 8 H: cyclopentane 2.5 ppm: t: 2 H: CH$_3$-CH$_2$-CH$_2$-CH$_2$- 7.5–8 ppm: m: 5 H: aromatic 5 ppm: s: 1 H: NH B) 2-n-Butyl-1-[(2'-carboxybiphenyl-4-yl)methyl]-5-(1 -cyano-1-phenylsulfonylmethylene)-4-spirocyclopentane-2-imidazoline The expected compound is prepared by following the method described in Example 9, steps B) and C). It crystallizes from an ether/hexane mixture.

M.p.$_c$=172° C.
Mass spectrum: MH$^+$: 568
NMR spectrum: 0.7 ppm: quint: 3 H: CH$_3$ (nBu) 1–1.4 ppm: m: 4 H: CH$_3$-CH$_2$-CH$_2$-CH$_2$- 1.6–2.6 ppm: m: 10 H: cyclopentane+CH$_3$-CH$_2$-CH$_2$-CH$_2$- 5.25 ppm: d: 2 H: -CH$_2$-C$_6$H$_4$- 5.6–7.7 ppm: m: 13 H: aromatic 12.7 ppm: s : 1 H: CO$_2$H The NMR spectrum indicates the presence of a mixture of the cis and trans forms of the methylene in equilibrium.

EXAMPLE 16

2-n-Butyl-5-[1-cyano-1-(3-trifluoromethylbenzoyl)methylene]-4-spirocyclopentane-1-[(2'-carboxybiphenyl-4-yl)methyl]-2-imidazoline trifluoroacetate

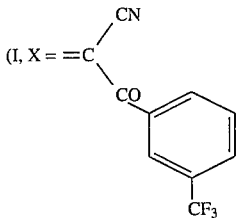

A) 2-n-Butyl-5-[1-cyano-1-(3-trifluoromethylbenzoyl)methylene]-4-spirocyclopentane-2-imidazoline This compound is prepared by reacting (3-trifluoromethylbenzoyl)acetonitrile with the compound prepared in Example 4, step A), following the method described in Example 9, step A). The product obtained is purified by chromatography on silica using a heptane/acetone mixture (9/1, v/v) as the eluent.

M.p.$_c$= 72°–75° C.
NMR spectrum: 0.8 ppm: t: 3 H: CH$_3$ (nBu) 1.25 ppm: sext: 2 H: CH$_3$-CH$_2$-CH$_2$-CH$_2$- 1.55 ppm: quint: 2 H: CH$_3$-CH$_2$-CH$_2$-CH$_2$- 1.6–2.4 ppm: m: 8 H: cyclopentane 2.6 ppm: t: 2 H: CH$_3$-CH$_2$-CH$_2$-CH$_2$- 7.6–8 ppm: m: 4 H: aromatic
IR (KBr): 2200 cm$^{-1}$ B) 2-n-Butyl-5-[1-cyano-1-(3-trifluoromethylbenzoyl)methylene]-4-spirocyclopentane-1-[(2'-carboxybiphenyl-4-yl)methyl]-2-imidazoline trifluoroacetate The expected compound was prepared by following the method described in Example 9, steps B) and C). This compound crystallizes from an ether/hexane mixture.

M.p.$_c$=62°–67° C.
NMR spectrum: 0.8 ppm: t: 3 H: CH$_3$ (nBu) 1.35 ppm: sext: 2 H: CH$_3$-CH$_2$-CH$_2$-CH$_2$- 1.60 ppm: quint: 2 H: CH$_3$-CH$_2$-CH$_2$-CH$_2$- 1.80–2.4 ppm: m: 8 H: cyclopentane 2.65 ppm: t: 2 H: CH$_3$-CH$_2$-CH$_2$-CH$_2$- 5 ppm: s: 2 H: -CH$_2$-C$_6$H$_4$- 6.8–7.8 ppm: m: 12 H: aromatic

What is claimed is:

1. A compound of formula (2)

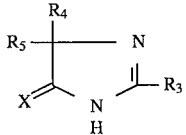

in which:

R$_3$ is a hydrogen, a C$_{1-6}$ alkyl which is unsubstituted or substituted by one or more halogen atoms, a C$_{2-6}$ alkenyl, a C$_{3-7}$ cycloalkyl, a phenyl, a phenylalkyl in which the alkyl is C$_1$–C$_3$, or a phenylalkenyl in which the alkenyl is C$_2$–C$_3$, said phenyl groups being unsubstituted or monosubstituted or polysubstituted by a halogen atom, a C$_{1-4}$ alkyl, a C$_{1-4}$ halogenoalkyl, a C$_{1-4}$ polyhalogenoalkyl, a hydroxyl or a $_{1-4}$ alkoxy;

R$_4$ and R$_5$ are each independently a C$_{1-6}$ alkyl, a C$_{3-7}$ cycloalkyl, a phenyl, or a phenylalkyl in which the alkyl is C$_{1-3}$, said alkyl, phenyl or phenylalkyl groups being unsubstituted or substituted by one or more halogen atoms or by a group selected from the group consisting of C$_{1-4}$ perfluoroalkyl, hydroxyl and C$_{1-4}$ alkoxy; or R$_4$ and R$_5$ together are a group of formula (CH$_2$)$_n$ or a group of formula (CH$_2$)$_p$ -Y(CH$_2$)$_q$, in which Y is an oxygen atom; a sulfur atom; a carbon atom substituted by a C$_{1-4}$ alkyl group, a phenyl, or a phenylalkyl in which the alkyl is C$_1$–C$_3$; or a group N-R$_6$ in which R$_6$ is a hydrogen, a C$_{1-4}$ alkyl, a phenylalkyl in which the alkyl is C$_1$–C$_3$, a C$_{1-4}$ alkylcarbonyl, a C$_{1-4}$ halogenoalkylcarbonyl, a C$_{1-4}$ polyhalogenoalkylcarbonyl, a benzoyl, an α-aminoacyl or an N-protecting group; or R$_4$ and R$_5$ together with the carbon atom to which they are bonded, form an indane or an adamantane;

p+q=m;

n is an integer between 2 and 11;

m is an integer between 2 and 5;

X is a group N-R$_7$ or a group C(CN)R$_8$,

R$_7$ is a C$_{1-4}$ alkyl or a cyano group;

R$_8$ is hydrogen, a cyano group, a tetrazolyl group, a tert-butyltetrazolyl group, a phenylsulfonyl group or a group COR$_9$; and R$_9$ is a thienyl, a furyl, a C$_{1-4}$ alkoxy, a phenoxy, a benzyloxy or a phenyl which is unsubstituted or substituted by a halogen, a C$_{1-4}$ alkyl or a C$_{1-4}$ polyhalogenoalkyl.

2. A compound of formula (2) as claimed in claim 11, wherein:

R$_3$ is a C$_{1-6}$alkyl;

R$_4$ and R$_5$ together with the carbon atom to which they are attached are a group of formula (CH$_2$)$_n$;

n is equal to 4 or 5;

X is a group C(CN)R$_8$;

R$_8$ is hydrogen, a cyano group, a tetrazolyl group, a tert-butyltetrazolyl group, a phenylsulfonyl group or a group COR$_9$; and R$_9$ is a thienyl, a furyl, a C$_{1-4}$ alkoxy, a phenoxy, a benzyloxy or a phenyl which is unsubstituted or substituted by a halogen, a C$_{1-4}$ alkyl or a C$_{1-4}$ polyhalogenoalkyl.

3. A compound as claimed in claim 2, which is 2-n-butyl-5-dicyanomethylene- 4-spirocyclopentane-2-imidazoline.

4. A compound as claimed in claim 2, which is 2-n-butyl-5-(1-cyano-1 -ethoxycarbonylmethylene)-4-spirocyclopentane-2-imidazoline.

5. A compound as claimed in claim 2, which is 2-n-butyl-5-(1-cyano-1-tert-butoxycarbonylmethylene)- 4-spirocyclopentane-2-imidazoline.

6. A compound as claimed in claim 2, which 5-(1-benzoyl-1-cyanomethylene)- 2-n-butyl-4-spirocyclopentane-2-imidazoline.

7. A compound as claimed in claim 2, which is 2-n-butyl-5-(1-cyano-1-methoxycarbonylmethylene)- 4-spirocyclopentane-2-imidazoline.

8. A compound as claimed in claim 2, which is 5-(1-benzyloxycarbonyl-1-cyanomethylene)- 2-n-butyl-4-spirocyclopentane-2-imidazoline.

9. A compound as claimed in claim 2, which is 2-n-butyl-5-[1-cyano-1-(fur-2-ylcarbonyl)methylene]-4-spirocyclopentane-2-imidazoline.

10. A compound as claimed in claim 2, which is 2-n-butyl-5-[1-cyano-1-(thien-2-ylcarbonyl)methylene]-4-spirocyclopentane-2-imidazoline.

11. A compound as claimed in claim 2, which is 2-n-butyl-5-[1,1-dicyanomethylene]-4-spirocyclopentane-2-imidazoline.

12. A compound as claimed in claim 2, which is 2-n-butyl-1-[(2'-dicyanobiphenyl-4-yl)methyl]-5-[1,1-dicyanomethylene]-4-spirocyclopentane-2-imidazoline.

13. A compound as claimed in claim 2, which is 2-n-butyl-5-(1-cyano-1-phenylsulphonylmethylene]-4-spirocyclopentane-2-imidazoline.

14. A compound as claimed in claim 2, which is 2-n-butyl-5-[1-cyano-(3-trifluoromethylbenzoyl)-methylene]-4-spirocyclopentane-2-imidazoline.

* * * * *